United States Patent
Chojnacki et al.

(10) Patent No.: US 7,695,682 B2
(45) Date of Patent: Apr. 13, 2010

(54) MIXING APPLIANCE PERTAINING TO A CHEMICAL OR BIOCHEMICAL ANALYSER AND COMPRISING A PIPETTE DRIVEN IN OSCILLATING MANNER

(75) Inventors: André Chojnacki, Saint-Gély du Fesc (FR); Jeanet Randrianarivo, Saint Martin de Londres (FR)

(73) Assignee: Maxmat SA, Grabels (FR)

( * ) Notice: Subject to any disclaimer, the term of this patent is extended or adjusted under 35 U.S.C. 154(b) by 1051 days.

(21) Appl. No.: 10/573,787

(22) PCT Filed: Oct. 13, 2004

(86) PCT No.: PCT/FR2004/002593

§ 371 (c)(1),
(2), (4) Date: Mar. 28, 2006

(87) PCT Pub. No.: WO2005/037417

PCT Pub. Date: Apr. 28, 2005

(65) Prior Publication Data

US 2007/0122312 A1    May 31, 2007

(30) Foreign Application Priority Data

Oct. 14, 2003  (FR) .................................. 03 11999

(51) Int. Cl.
  *B01L 3/02*  (2006.01)
  *B01F 7/00*  (2006.01)
(52) U.S. Cl. ................. 422/100; 73/863.32; 73/864; 366/194; 366/195; 366/196; 366/243; 366/244; 366/247; 366/249; 366/250; 366/251
(58) Field of Classification Search ................. 422/100; 73/863.32, 864; 366/167.1, 167.2, 168.1, 366/168.2, 169.1, 194–196, 243–244, 247, 366/249–251
See application file for complete search history.

(56) References Cited

U.S. PATENT DOCUMENTS

| 3,780,992 | A |   | 12/1973 | Nishi et al. |           |
|-----------|---|---|---------|--------------|-----------|
| 3,955,802 | A | * | 5/1976  | de Bruyne    | 366/343   |
| 4,046,515 | A | * | 9/1977  | de Leeuw     | 422/100   |
| 4,343,766 | A | * | 8/1982  | Sisti et al. | 422/63    |
| 4,473,299 | A | * | 9/1984  | Guibert      | 366/76.4  |
| 4,499,053 | A | * | 2/1985  | Jones        | 422/68.1  |

(Continued)

FOREIGN PATENT DOCUMENTS

JP     A 60 257826     12/1985

*Primary Examiner*—Brian R Gordon
(74) *Attorney, Agent, or Firm*—Oliff & Berridge, PLC (57) ABSTRACT

The invention relates to a mixing appliance pertaining to a chemical or biochemical analyser and comprising a pipette having a head, a body and a free end. The head of the pipette is fixed to a head supporting block. The inventive mixing appliance comprises driving elements for triggering the oscillation of the free end of the pipette. Said driving elements consist of an actuating unit that is fixed to a frame, both elements being associated with a guiding block provided with an eccentric block that is mounted in such a way as to rotate freely about an axis and is in contact with the body of the pipette. The head supporting block is mounted in such a way as to rotate freely in the frame about an axis perpendicular to the plane in which the pipette oscillates.

6 Claims, 11 Drawing Sheets

U.S. PATENT DOCUMENTS

| | | | | |
|---|---|---|---|---|
| 4,570,495 A | * | 2/1986 | Terada | 73/864.25 |
| 4,869,114 A | * | 9/1989 | Kido et al. | 73/864.24 |
| 5,941,636 A | * | 8/1999 | Lu | 366/249 |
| 6,447,728 B1 | * | 9/2002 | Wilmes et al. | 422/100 |
| 6,866,820 B1 | * | 3/2005 | Otto et al. | 422/63 |
| 7,361,308 B2 | * | 4/2008 | Fagerstam | 422/99 |
| 2002/0110493 A1 | * | 8/2002 | Dales et al. | 422/100 |

* cited by examiner

MIXING APPLIANCE PERTAINING TO A CHEMICAL OR BIOCHEMICAL ANALYSER AND COMPRISING A PIPETTE DRIVEN IN OSCILLATING MANNER

BACKGROUND OF THE INVENTION

The invention relates to a mixing appliance pertaining to a chemical or biochemical analyser comprising at least one pipette having a body, a free end and a head fixed to a head supporting block, and driving means designed to cause oscillation of the free end of the pipette, the driving means comprising an actuating unit securely fixed to a frame and associated with a guiding block operating in conjunction with the body of the pipette.

STATE OF THE ART

A chemical or biochemical analyser is composed of several modules in particular comprising a mixing appliance to mix a sample and a reactant. In a known calorimetry-based chemical or biochemical analyser, a reaction chamber of tapered shape presents walls made of transparent material having a volume generally smaller than 500 µl. Analysis is then performed by optic reading, by transparency through the bottom wall of the chamber and the surface of the meniscus of the reactive medium. It is also possible to use a chamber of rectangular cross-section and to use horizontal optic reading through the vertical walls of the chamber. This enables problems relating to the meniscus and to the presence of bubbles to be eliminated, but the sedimentation effects, in a not very efficient mixing, remain crucial.

The mixing appliance of a chemical or biochemical analyser has to meet several basic requirements to obtain optimum mixing of the reactive medium:
- a repeatable system: the design of the mixing appliance must take account of minimization of the disturbance effects when consecutive mixings are performed.
- a reproducible system: replacement of the pipette, if and when necessary, must be able to be performed by the user and must preserve the stirring characteristics. Attention moreover has to be paid to the stability of the characteristics of the mixing appliance over time.
- minimum contamination: the reactive medium must only be in contact with a reduced number of elements and each of these elements must present a minimum roughness-free surface.
- efficient mixing: the quality of mixing influences the repeatability of the results directly. This is why it is indispensable to be able to adjust the stirring parameters.
- no bubbles: bubbles result from a cavitation phenomenon caused by contact between the mixing element, for example a pipette, and the reactive medium. Factors such as the stirring speed, stirring amplitude, and viscosity of the reactive medium have to be able to be adjusted.
- for analysers using optic measurements, in particular by transparency through the reactive medium, preserving the symmetry of shape of the meniscus: as an ideally symmetric meniscus ensures optimum propagation of the light beam, the mixing system must preserve this geometry.

Several different types of mixing appliance exist that are able to be associated with a chemical or biochemical analyser: electromagnet mixing appliance, rotary mixing appliance, or piezoelectric mixing appliance. The document WO-A-01/36892 describes a mixing appliance generating a beating movement of the pipette. The mechanical vibrations are generated by an electro-magnet the supply whereof causes an alternating oscillation movement of the pipette to perform mixing of the reactive medium. The forced oscillation frequency of the pipette is adjustable by the supply of the electro-magnet. Thus, this appliance, like known appliances, uses the return force of the pipette, i.e. the pipette is stressed and its flexibility is used to obtain oscillations. The pipette is actuated a first time, for example by an electromagnet, and it is because it is stressed that it continues to oscillate. The pipette therefore operates in forced oscillation, which increases the friction on the pipette and the sensitivity around the resonance zone of the oscillations. This then results in wear of the pipette and poor mixing conditions.

OBJECT OF THE INVENTION

The object of the invention is to provide an appliance that does not present these shortcomings and, in particular, a mixing appliance of a chemical or biochemical analyser enabling efficient mixing to be achieved, without creating bubbles, and with the shape of the meniscus of the reactive mixture being preserved.

According to the invention, this object is achieved by an appliance according to the appended claims, and more particularly by the fact that the head supporting block is mounted in such a way as to rotate freely in the frame around an axis perpendicular to the plane in which the pipette oscillates.

According to a development of the invention, the guiding block comprises a connecting block, securely fixed to the axis of the actuating unit, and an eccentric block, securely fixed to the connecting block, in contact with the body of the pipette, and mounted in such a way as to rotate freely around its axis.

BRIEF DESCRIPTION OF THE DRAWINGS

Other advantages and features will become more clearly apparent from the following description of particular embodiments of the invention given as non-restrictive examples only and represented in the accompanying drawings, in which.

DESCRIPTION OF PARTICULAR EMBODIMENTS

Figure 1:
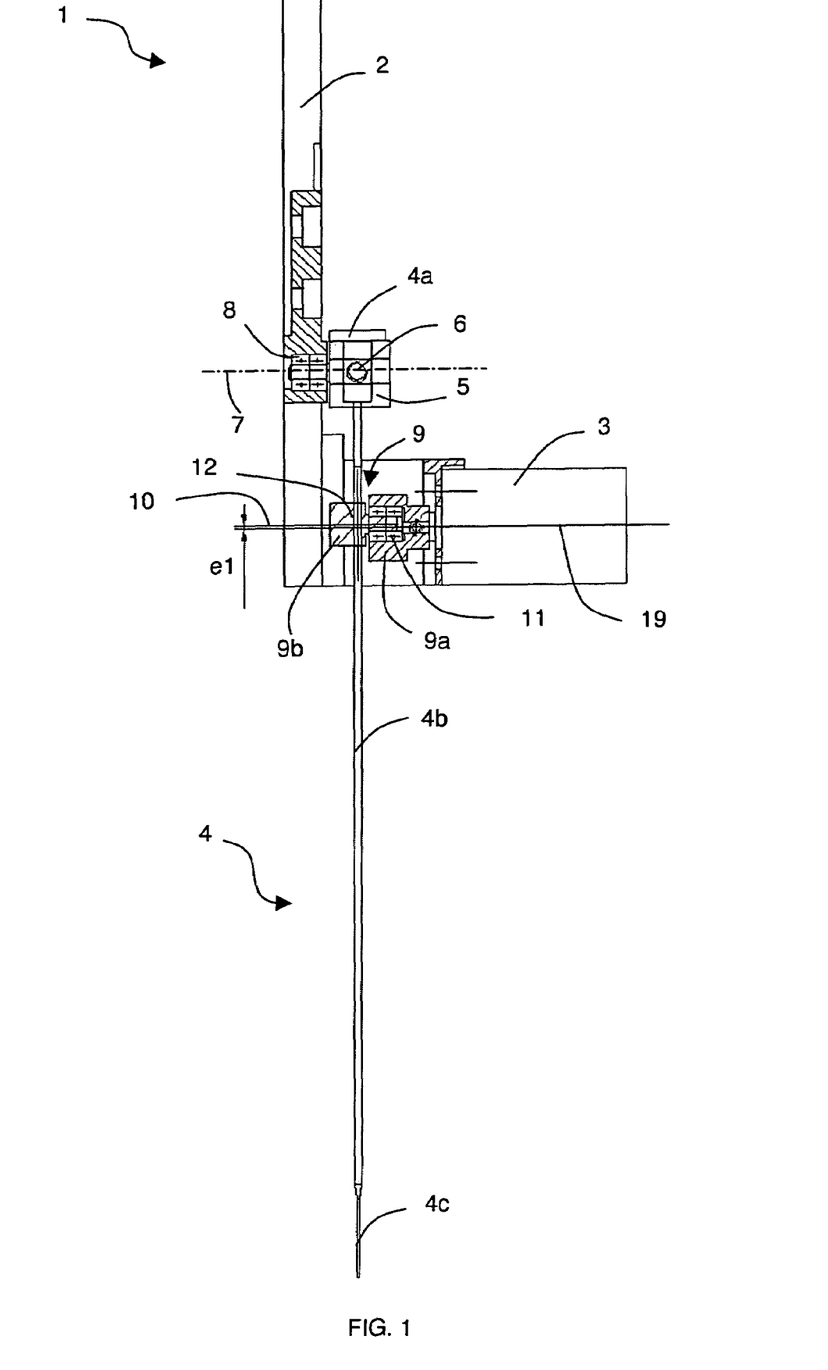
FIG. 1 is a side view, in cross-section, of a particular embodiment of a mixing appliance according to the invention.

In FIG. 1, the mixing appliance 1 comprises a frame 2 on which there is fixed an actuating unit 3, preferably constituted by a DC motor, notably comprising means for regulating the speed, acceleration and/or operating time. The mixing appliance 1 conventionally comprises a pipette 4 having a head 4a, a body 4b and a free end 4c. The head 4a of the pipette 4 is fixed to a head supporting block 5 by any suitable securing means, for example by a clamping screw 6. The head supporting block 5 is mounted rotating freely in the frame 2 around an axis 7, for example by means of a set of bearings 8 fitted inside the frame 2. The bearings 8 can for example be ball-bearings or roller bearings. A guiding block 9 for the body 4b of the pipette 4 is securely fixed to the driving unit 3. The guiding block 9 comprises a connecting block 9a fitted on the axis 19 of the driving unit 3 by any suitable securing means, for example by a clamping screw, and an eccentric block 9b. The connecting block 9a and the driving unit 3 are coaxial. The eccentric block 9b is securely fixed to the connecting block 9a and mounted rotating freely around an axis 10, parallel to the axis 19, by means of a set of bearings 11, fitted inside the connecting block 9a. In the particular embodiment represented in FIGS. 1 to 11, the body 4b of the pipette 4 passes right through the eccentric block 9b. The eccentric block 9b therefore comprises a bore 12 designed to enable the body 4b of the pipette 4 to slide freely with clearance. The driving unit 3, the head supporting block 5 and the pipette 4 are preferably located on the same side of the frame 2, as represented in FIG. 1.

Figure 2:
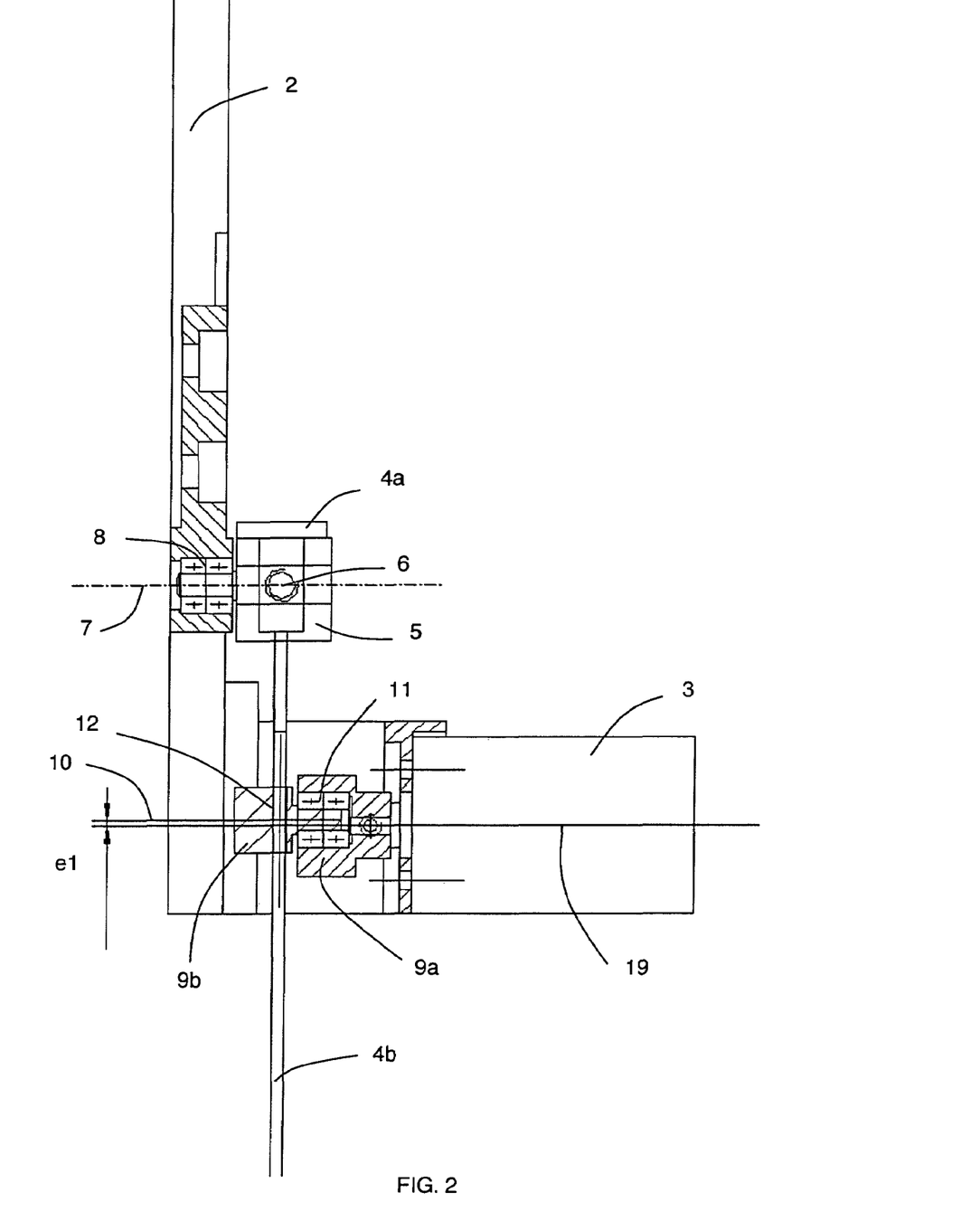
FIG. 2 is a partial enlarged scale view of the top part of the mixing appliance according to FIG. 1.

FIG. 2, which is an enlarged scale view of the top part of the mixing appliance 1 according to FIG. 1, enables the particular embodiment represented in FIG. 1 to be seen with greater precision. Indeed, the axis 10 of the eccentric block 9b is offset with respect to the axis 19 of the driving unit 3 by a value e1 of about 0.1 mm. The offset between the axes of the eccentric block 9b and of the connecting block 9a is therefore very small. This type of chemical or biochemical analyser is in fact designed for analysing minute quantities of product and the mixing appliance 1 is designed to mix in a reactive medium 13 the quantity whereof does not exceed one or two drops.

Figure 3:
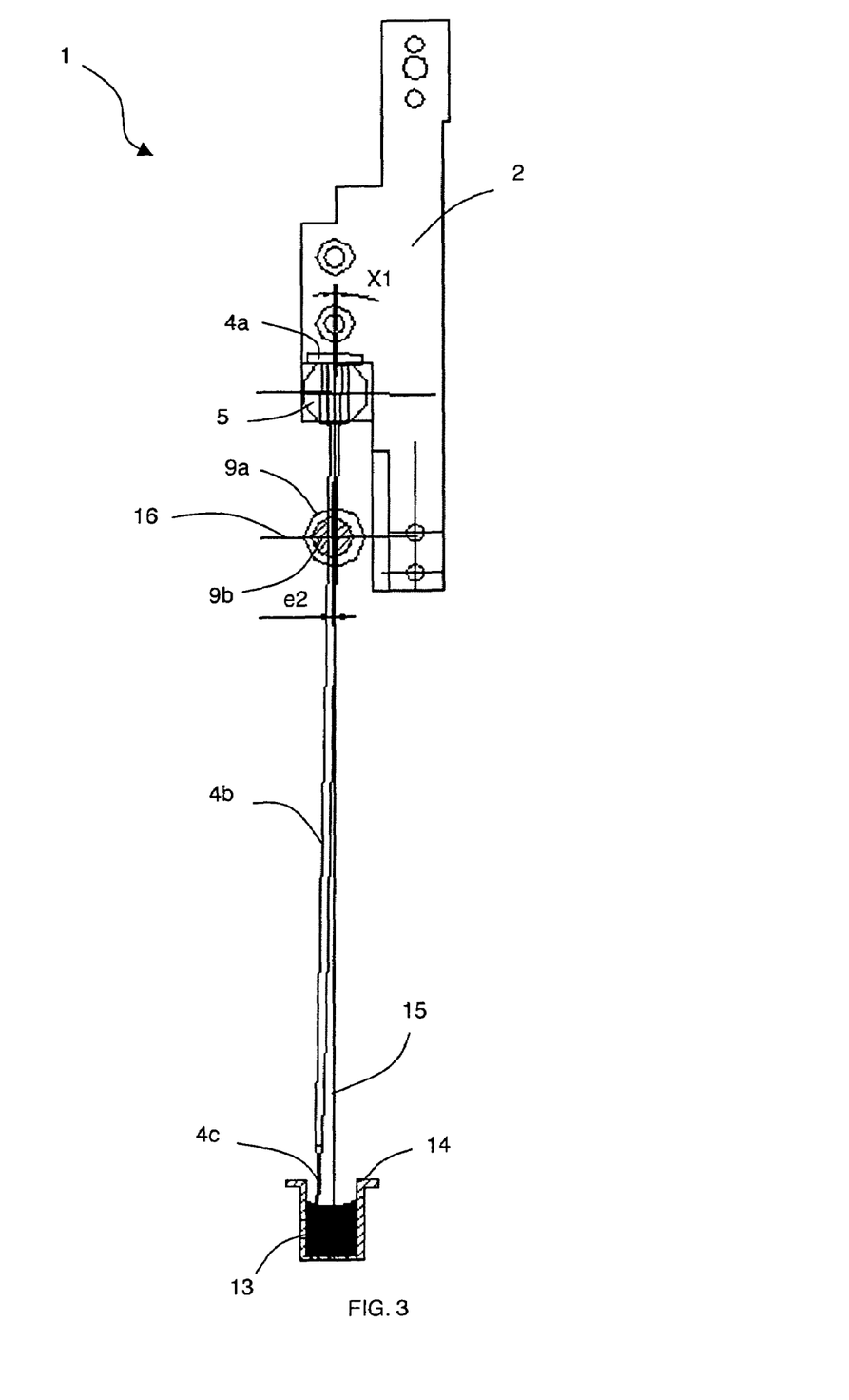
FIGS. 3 and 4 represent, in side view, the mixing appliance according to FIG. 1, illustrating the oscillation plane of the pipette in operation.
Figure 4:
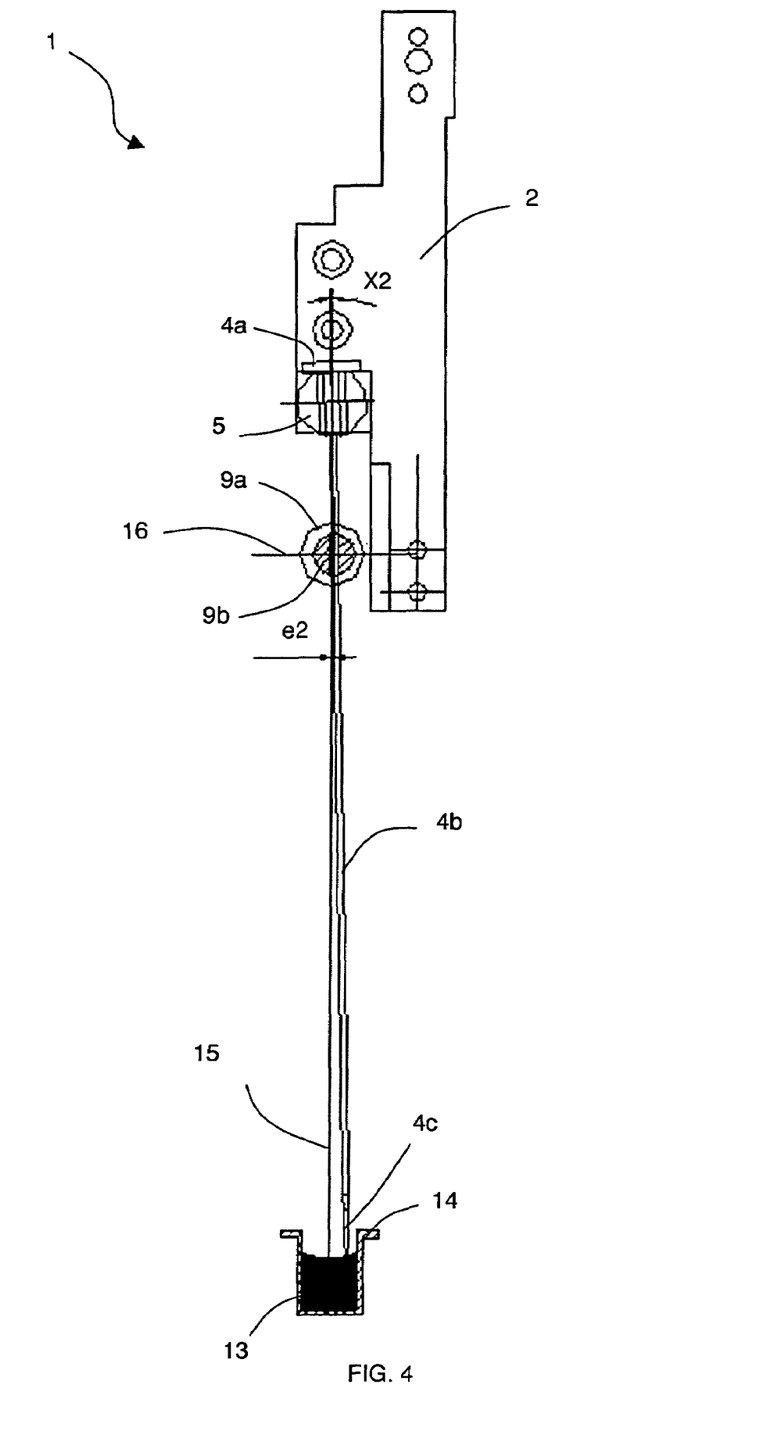

As shown in FIGS. 3 and 4, the reactive medium 13 is contained in a recipient 14 of small dimensions. These two figures represent the plane, perpendicular to the plane of FIG. 1, in which the pipette oscillates when the mixing appliance 1 operates. A vertical axis 15, associated with a horizontal axis 16, represent the reference axes of the connecting block 9a. The axis of rotation 19 of the connecting block 9a, which is also that of the driving unit 3, is perpendicular to the oscillation plane of the pipette 4 described above. The axes 15 and 16 and the axis of rotation 19 of the connecting block 9a therefore form the reference axes of the connecting block 9a.

FIGS. 3 and 4 represent first and second limit positions which the free end 4c of the pipette 4 can take so as not to come into contact with the recipient 14, respectively to the left and to the right in FIGS. 3 and 4. The amplitude of movement does not exceed a value e2 of about 0.1 mm, at the level of the axis 16, on each side of a central position, to obtain optimum mixing characteristics. In the figures, this central position is symbolized by the vertical axis 15. The small value of the eccentricity due to the eccentric block 9b therefore enables the reactive medium 13 to be mixed while preserving optimum mixing characteristics, in particular a minimum contamination, an absence of bubbles and a good reproducibility.

Figure 5:
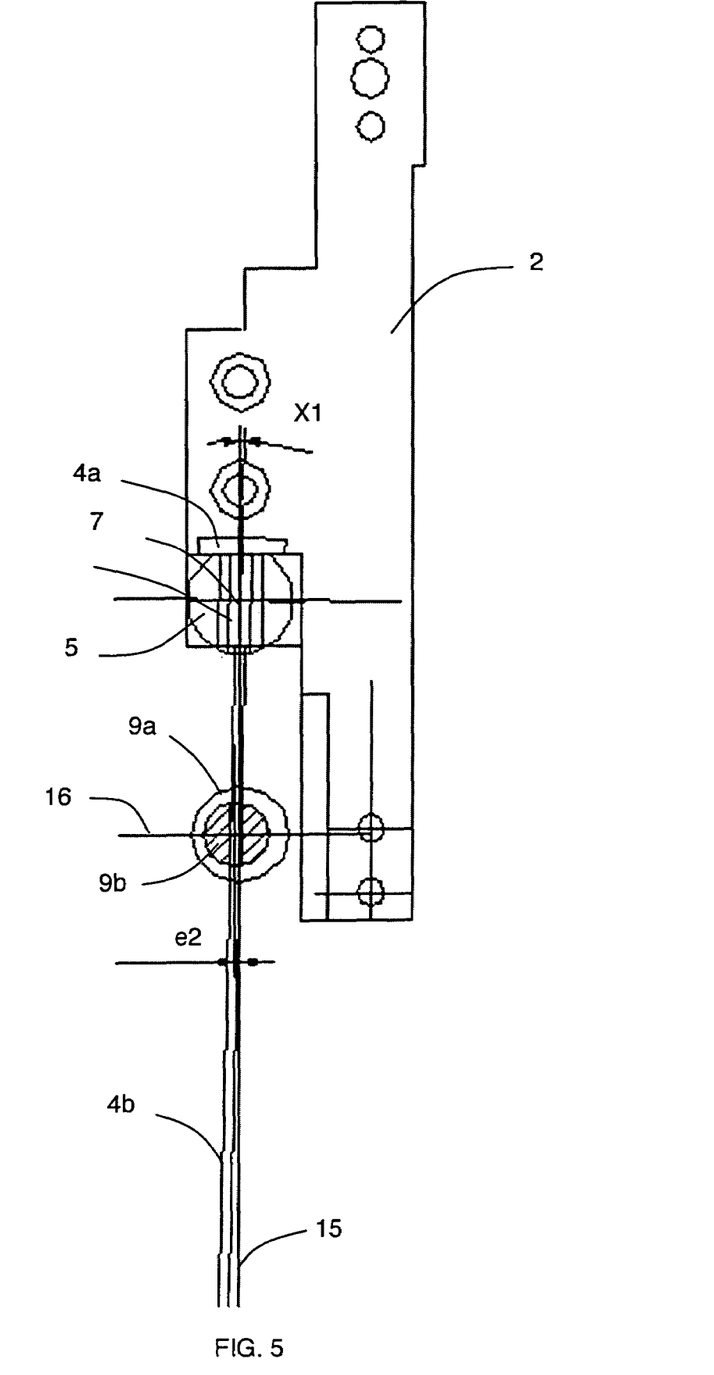
FIGS. 5 to 7 are partial enlarged scale views of the top part of the mixing appliance according to FIG. 1, represented without the driving block, and illustrating, in side view, three characteristic positions of the pipette, respectively to the left, in the centre and to the right.
Figure 6:
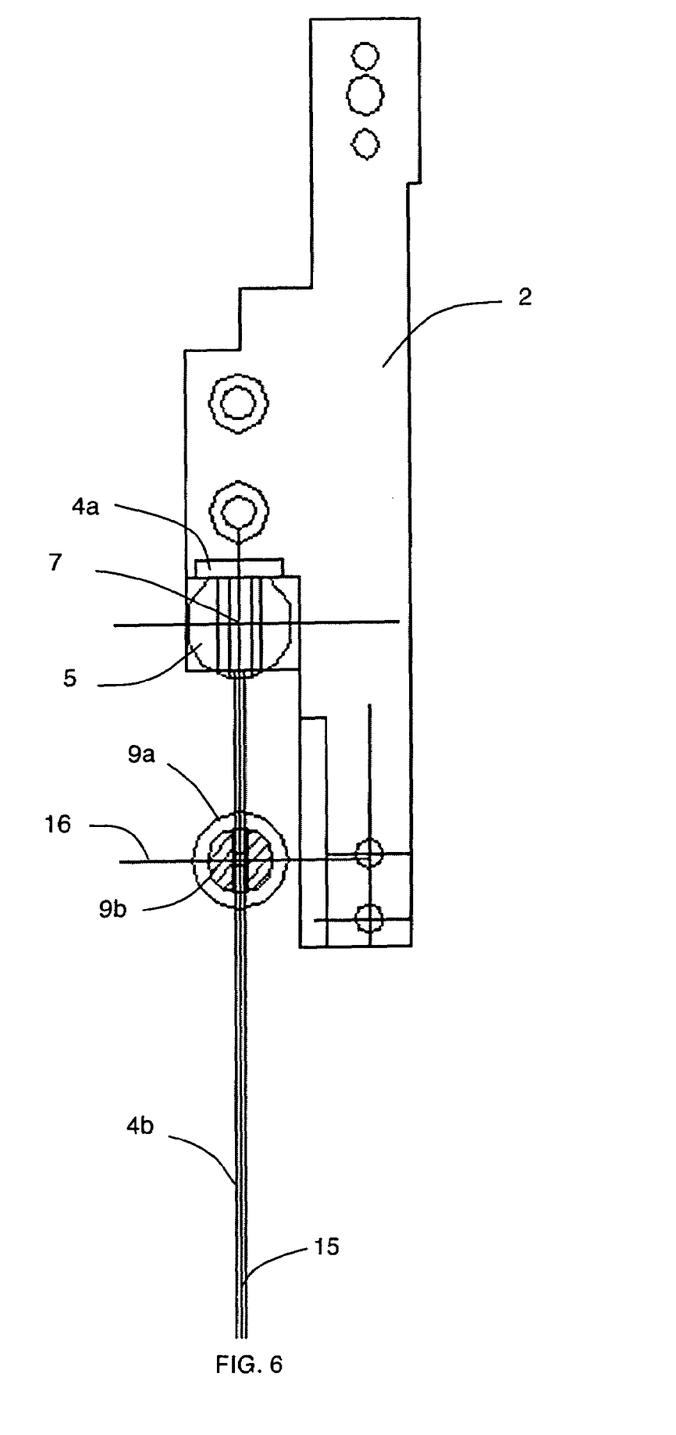
Figure 7:
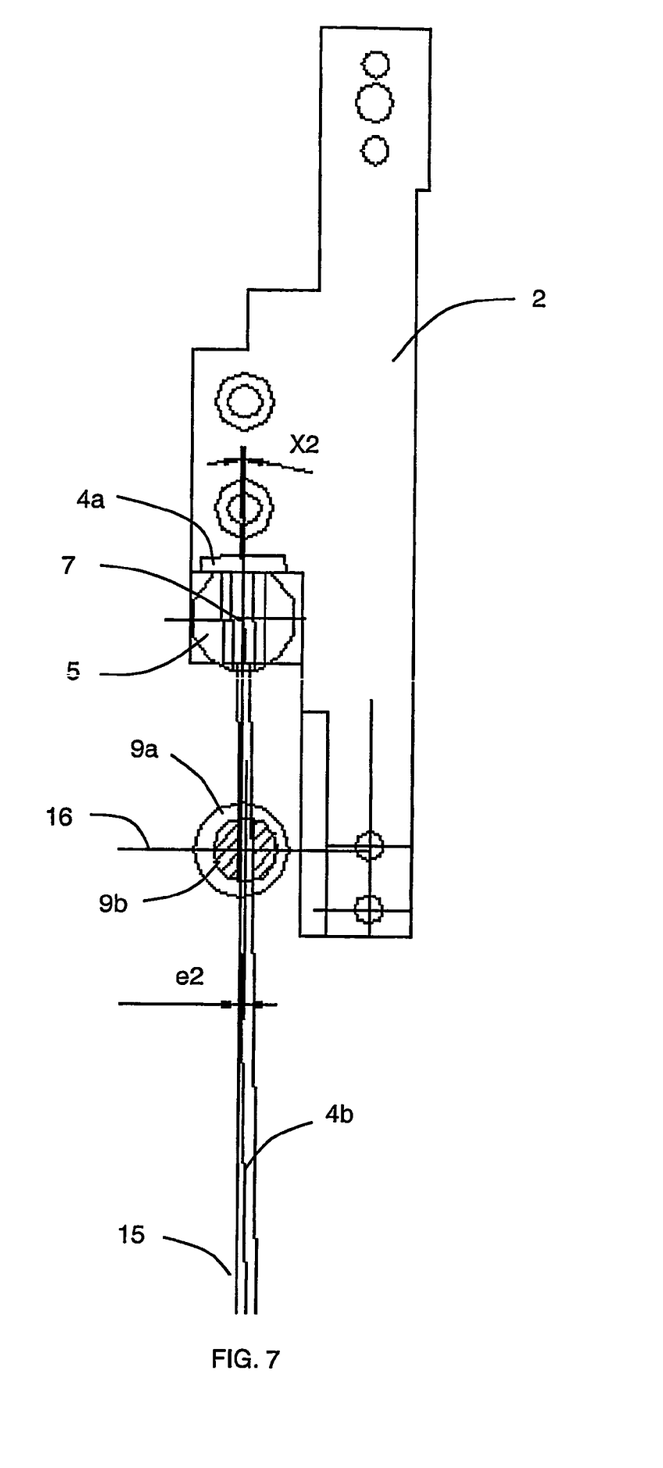

FIGS. 5 to 7 represent a partial enlarged scale side view of the top part of the mixing appliance 1 according to FIGS. 3 and 4. For a better readability and a better understanding, the driving unit 3, recipient 14 and reactive medium 13 have been removed. Thus, the FIG. 5 represents the left-hand limit position of the pipette 4 in its oscillation plane. This oscillation plane is parallel to the frame 2 and perpendicular to the axis 19 of the connecting block 9a and of the driving unit 3 and therefore to the axis 10 of the eccentric block 9b. As illustrated in FIG. 5, in its left-hand limit position, the centre of the eccentric block 9b is offset to the left with respect to the vertical axis 15 of the connecting block 9a, along the horizontal axis 16. The offset value is for example about 0.1 mm. The pipette 4, securely fixed to the head supporting block 5, which has performed a rotation to the right around its axis 7, perpendicular to the oscillation plane of the pipette 4, forms a first angle X1 with the vertical reference axis 15.

FIG. 6 represents the central position of the pipette 4 in its oscillation plane. In its central position, the centre of the eccentric block 9b is not offset with respect to the vertical reference axis 15. Likewise, the body 4b of the pipette 4 is aligned with the vertical axis 15. And the head supporting block 5 is in a central position.

FIG. 7 represents the right-side limit position of the pipette 4 in its oscillation plane. In this limit position, the centre of the eccentric block 9b is offset to the right with respect to the vertical axis 15, along the horizontal axis 16. The offset value is substantially the same as in the left-hand limit position. The head supporting block 5 has performed a rotation to the left around its axis 7 and the pipette 4 forms a second angle X2, opposite to the first angle but of substantially identical value, with the vertical reference axis 15.

Operation of the mixing appliance will be described in greater detail with respect to FIGS. 8 to 11. The driving unit 3 is preferably equipped with a system for regulating the speed, acceleration and/or operating time. Initially, in the position represented in FIG. 8, it starts rotating in the direction of the arrow R, at a given speed corresponding to the mixing intensity to be transmitted to the reactive medium 13. It then drives the connecting block 9a, securely fixed to the axis 19 of the driving unit 3. The connecting block 9a, coaxial with the driving unit 3, therefore rotates on itself around the axis 19 of the driving unit 3. As described above, the eccentric block 9b, securely fixed to the connecting block 9a, is mounted such as to rotate freely around its axis 10, offset by a value e1 with respect to the axis 19, inside the connecting block 9a. What is meant by eccentric block is any part the function whereof is to transform a continuous circular movement into an alternating straight movement. The connecting block 9a, by means of the axis 19 of the driving unit 3, is therefore animated by a uniform circular movement. It then drives the eccentric block 9b in rotation around the axis 19. The eccentric block 9b on the other hand, mounted such as to rotate freely around its axis 10, and wherethrough the body 4b of the pipette 4 passes, performs a rotation of an angle X1 around its axis 10. The eccentric block 9b thus causes pivoting of the pipette 4 around the axis 7, the body 4b of the pipette 4 sliding in the bore 12 of the eccentric block 9b. The mixing appliance 1 is then in the left-hand limit position represented in FIG. 9, in which the pipette 4 makes an angle X1 with the vertical axis 15 (FIG. 5).

Figure 8:
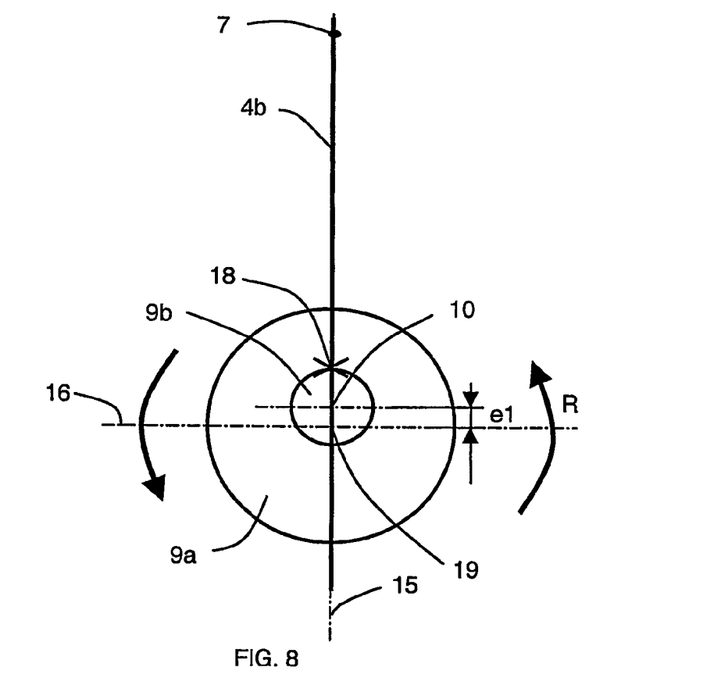
FIGS. 8 to 11 represent, in side view, a schematic view of the four positions of the guiding block of a mixing appliance according to FIG. 1.

In FIGS. 8 to 11, the position of a point 18 of the pipette 4 is symbolized by a cross. The distance between the axis 7 and the point 18 always remains constant. In FIG. 8, the point 18 is situated at the intersection of the wall of the eccentric block 9b with the vertical axis 15.

Figure 9:
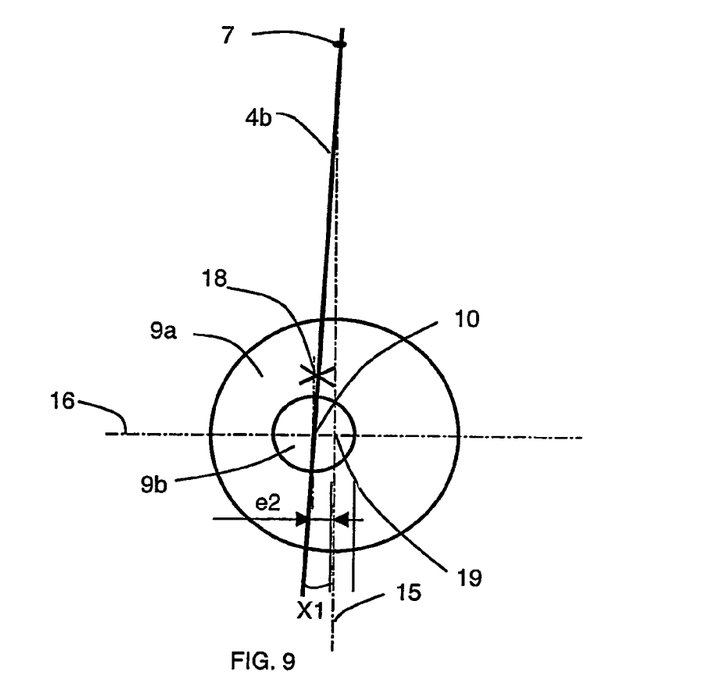
Figure 10:
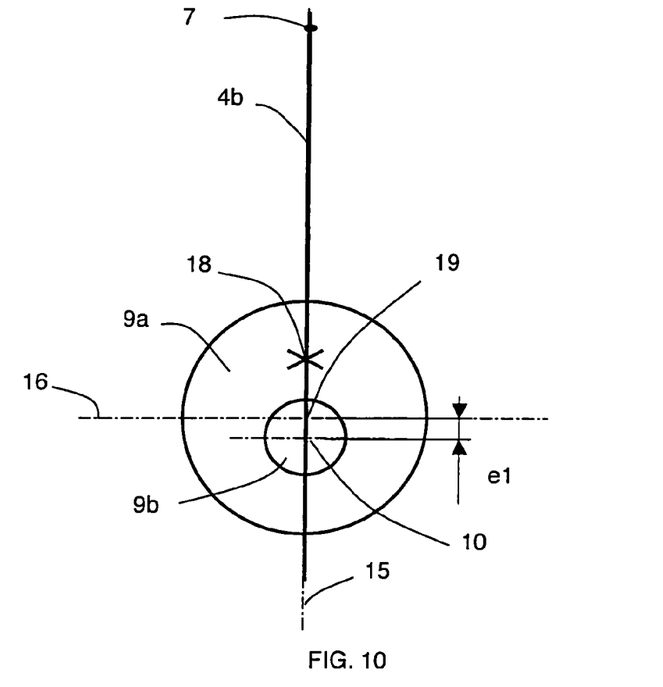
Figure 11:
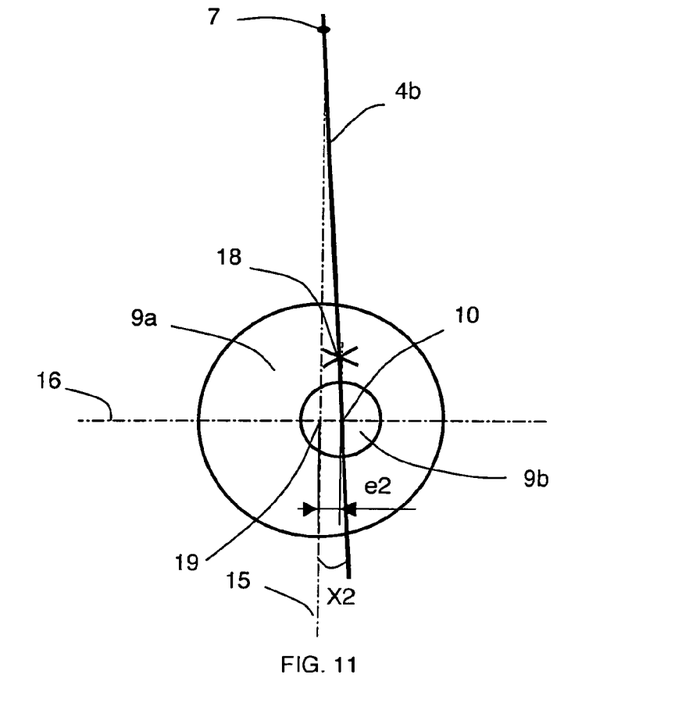

When the pipette 4 has reached its left-hand limit position represented in FIG. 9, the point 18 is therefore no longer in contact with the eccentric block 9b, which illustrates the sliding phenomenon, and the body 4b of the pipette 4 forms an angle X1 with the vertical axis 15. The axis 10 is offset by a value e2 with respect to the vertical axis 15.

Then the connecting block 9a continues its rotation around the axis 19 and the eccentric block 9b, driven by the connecting block 9a, performs a rotation of angle X1, of substantially the same value, around its axis 10. The eccentric block 9b thus causes pivoting of the pipette 4 around the axis 7, the body 4b of the pipette 4 sliding in the bore 12 of the eccentric block 9b. The mixing appliance 1 is then in the central position represented in FIG. 10, in which the eccentric block 9b is below the axis 16, offset by a value e1, but is aligned with the vertical axis 15. In this central position, different from the one represented in FIG. 8, the point 18 is not in contact with the eccentric block 9b, which illustrates the sliding phenomenon, and the body 4b of the pipette 4 is aligned with the vertical axis 15.

Then the connecting block 9a continues its rotation around its axis 19 and the eccentric block 9b, driven by the connecting block 9a, performs a rotation of angle X2 around its axis 10. The eccentric block 9b thus causes pivoting of the pipette 4 around the axis 7, the body 4b of the pipette 4 sliding in the bore 12 of the eccentric block 9b. The mixing appliance 1 is then in the right-hand limit position represented in FIG. 11, in which the pipette 4 makes an angle X2 with the vertical axis 15 (FIG. 7). When the pipette 4 has reached its right-hand limit position represented in FIG. 11, the point 18 is not in contact with the eccentric block 9b, which illustrates the sliding phenomenon, and the body 4b of the pipette 4 forms an angle X2 with the vertical axis 15. The axis 10 is offset by a value e2 with respect to the vertical axis 15.

Finally, the connecting block 9a continues its rotational movement and the eccentric block 9b, driven by the connecting block 9a, performs a rotation of angle X2, substantially of the same value, to revert to its initial position represented in FIG. 8.

The sequence of positions described above corresponds to a full rotation of the connecting block 9a. This full rotation thus causes a to-and-fro movement of the pipette 4. Repetition of this cycle generates repetition of the to-and-fro movement thus generating a pendulous movement.

Figure 12:
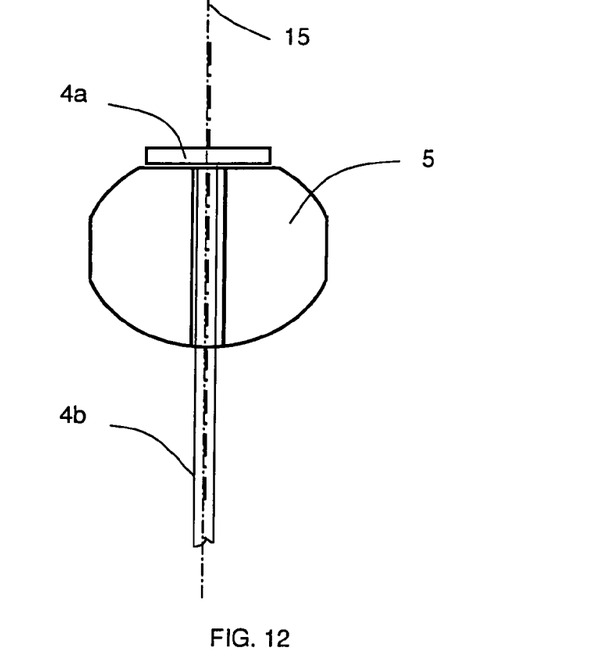
FIGS. 12 to 14 represent, in schematic and exaggerated manner, in. partial enlarged scale side view, three positions of the head supporting block in operation of a mixing appliance according to FIGS. 3 and 4.
Figure 13:
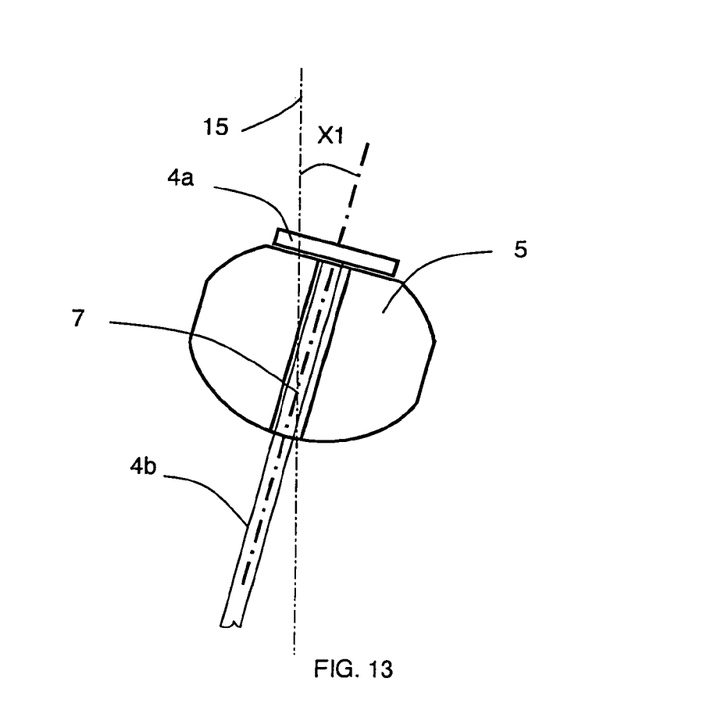
Figure 14:
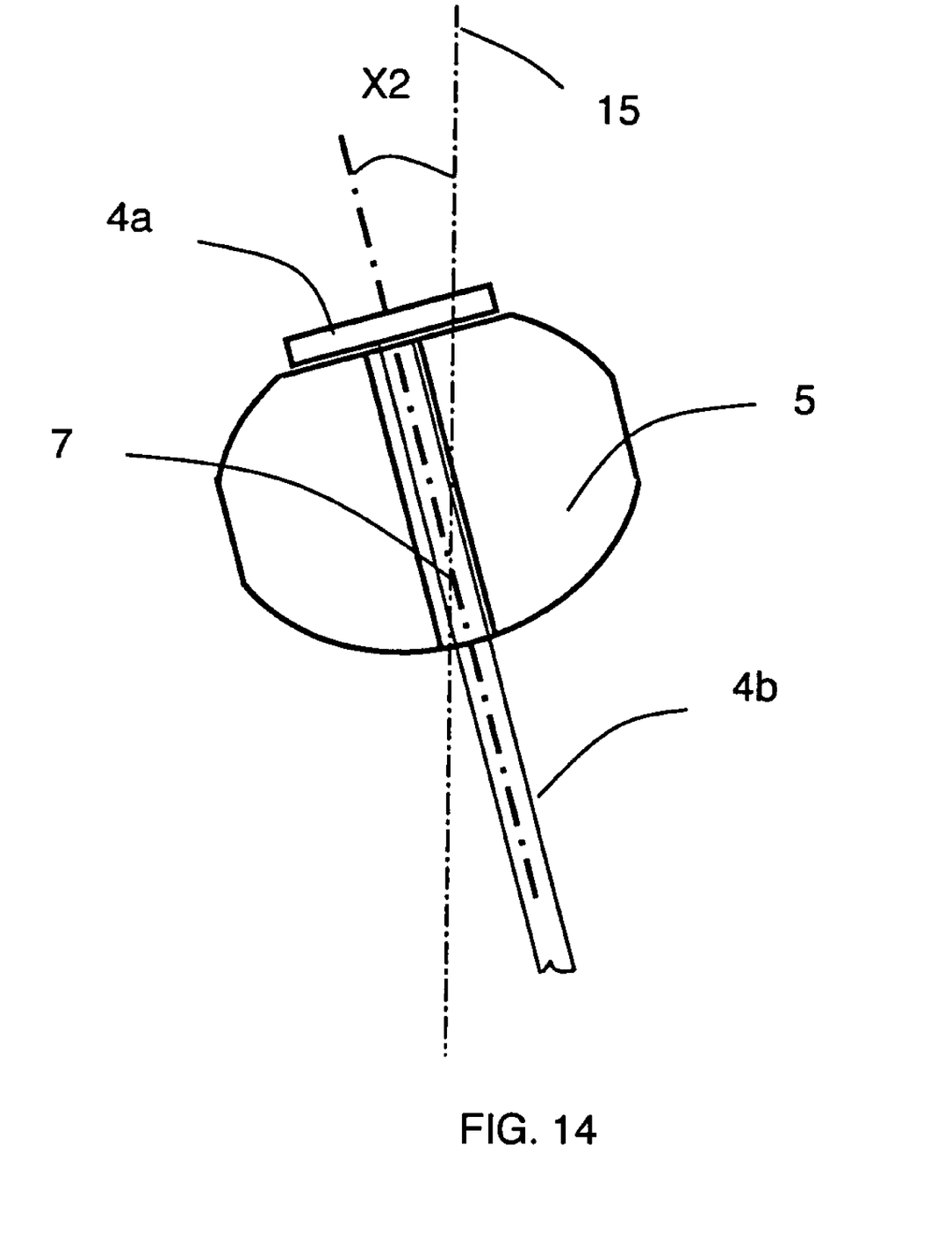

For a better understanding of operation, FIGS. 12 to 14 illustrate in exaggerated manner the variations of the angle X formed by the head supporting block 5 and the pipette 4 with the vertical axis 15. FIG. 12 represents the initial central position of the pipette 4, in which the pipette 4 is vertical (FIG. 6). FIG. 13 represents the left-hand limit position of the pipette 4, in which the pipette 4 forms the first angle X1 with the vertical axis 15 (FIG. 5). FIG. 14 represents the right-hand limit position of the pipette 4, in which the pipette 4 forms the second angle X2, opposite to the first angle but substantially of the same value, with the vertical axis 15 (FIG. 7).

In practice, it is not recommended to adjust the eccentric according to the required amplitude of movement of the free end 4c of the pipette 4. Indeed, it is preferable to fix the eccentric block 9b onto the connecting block 9a once and for all so as to then avoid any mechanical handling which would result in problems, notably repeatability problems. This is why a regulating system (not represented) of the driving unit 3 is desirable. The speed, acceleration and/or operating time of the motor can be regulated. Possible resonance phenomena of the pipette 4 at certain moments of its pendulous movement can thus be eliminated or reduced by adjusting the acceleration and deceleration of the motor. This enables mixings of different intensities and durations to be performed, without any mechanical adjustment of the pipette 4 or of the eccentric block 9b, while preserving optimum mixing characteristics.

In a preferred embodiment, the distance separating the axis 7 of the head supporting block 5 and the free end 4c of the pipette 4 is about 126.25 mm and the distance between the axis 7 of the head supporting block 5 and the axis of the driving unit 3 is about 23.75 mm. The vertical axis of the pipette 4 in the central position is separated from the frame 2 by a distance of about 5 mm.

Thus, the eccentric block 9b transforms the rotational movement of the connecting block 9a into a to-and-fro movement of the pipette 4 that can be assimilated to a pendulous movement. This pendulous movement is ensured by the fact that the head 4a of the pipette 4 is fixed to a head supporting block 5, which itself is not fixed with respect to the frame 2, but mounted such as to rotate freely around its axis 7, for example by means of bearings 8 fitted inside the frame 2. Thus, when the body 4b of the pipette 4 is driven by the eccentric block 9b and slides in the bore 12, the head 4a of the pipette 4, fixed to the head supporting block 5, at the same time performs a rotation around the axis 7. It is therefore the combination of these two movements that forms the pendulous movement which presents the following advantages over known mixing appliances:

- the low friction on the body 4b of the pipette 4 allows mixing frequencies of more than 100 Hz for an enhanced mixing efficiency.
- the pendulous configuration does not use the stiffness of the pipette 4 to work in forced oscillation and enables operation in a wider frequency range.
- the bearing parts 8 and 11 have an enhanced lifetime due to the low friction.
- repeatability is increased due to the low friction.
- reproducibility is improved as operation of the mixing appliance 1 hardly depends on the characteristics of the pipette 4.
- replacement of the pipette 4 does not require any special qualification.

The performances of a pendulous-drive mixing appliance are improved by a factor of more than 3 compared with those of an electro-magnet mixing appliance.

The invention is not limited to the embodiments described above. In particular, the driving unit can be replaced by any type of actuating unit.

The body 4b of the pipette 4 may not slide in the eccentric block 9b but simply remain in contact with an eccentric block. The latter can advantageously comprise a set of ball-bearings. A calibrated spring then ensures contact of the pipette 4 with the ball-bearings. This arrangement enables any friction induced by the eccentric block to be eliminated.

The invention claimed is:

1. A mixing appliance for use with a chemical or biochemical analyser, the mixing appliance comprising:
   a frame;
   a head supporting block freely rotatably disposed within the frame;
   at least one pipette including a body, a free end, and a head fixed to the head supporting block; and
   a driving unit disposed on the frame to cause the free end of the at least one pipette to oscillate within a plane, the supporting block being rotatable about an axis that is perpendicular to the plane, the driving unit including:
      an actuating unit fixed to the frame; and
      a guiding block located between the free end and the head of the pipette.

2. The mixing appliance according to claim 1, wherein the guiding block comprises:
   a connecting block, disposed along an axis of the actuating unit, and
   an eccentric block, fixed to the connecting block and in contact with the body of the pipette and mounted such as to rotate freely around an axis of the eccentric block.

3. The mixing appliance according to claim 2, wherein the body of the pipette extends through the eccentric block.

4. The mixing appliance according to claim 2, wherein the axis of the eccentric block is offset about 0.1 mm from the axis of the actuating unit.

5. The mixing appliance according to claim 1, wherein the actuating unit is a DC motor.

6. The mixing appliance according to claim 5, wherein the actuating unit comprises means for regulating at least one of speed, acceleration and operating time of the motor.

* * * * *